US010329427B2

(12) United States Patent
Sirota (10) Patent No.: US 10,329,427 B2
(45) Date of Patent: Jun. 25, 2019

(54) SELECTION AND BLENDING OF FEEDS FOR ASPHALT MANUFACTURE (71) Applicant: ExxonMobil Research and Engineering Company, Annandale, NJ (US)

(72) Inventor: Eric B. Sirota, Flemington, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/984,850

(22) Filed: May 21, 2018

(65) Prior Publication Data
US 2018/0265703 A1 Sep. 20, 2018

Related U.S. Application Data (62) Division of application No. 14/576,281, filed on Dec. 19, 2014, now Pat. No. 10,005,907.
(Continued)

(51) Int. Cl.
C08L 95/00 (2006.01)
C10C 3/00 (2006.01)
(Continued)

(52) U.S. Cl.
CPC .............. *C08L 95/00* (2013.01); *C08J 3/005* (2013.01); *C10C 3/005* (2013.01);
(Continued)

(58) Field of Classification Search
CPC ........ C08L 95/00; C08L 2555/10; C08J 3/005; C08J 2495/00; C08J 2395/00; C10C 3/00;
(Continued)

(56) References Cited

U.S. PATENT DOCUMENTS 1,782,186 A * 11/1930 Abson ...................... C10C 3/04
208/5
3,986,887 A * 10/1976 Pitchford ................ C08L 95/00
106/273.1
(Continued)

FOREIGN PATENT DOCUMENTS

CN 101694450 A 4/2010
EP 2071329 A2 6/2009
(Continued)

OTHER PUBLICATIONS

The International Search Report and Written Opinion of PCT/US2014/071342 dated Apr. 10, 2015.

*Primary Examiner* — Alexandra M Moore
(74) *Attorney, Agent, or Firm* — Scott F. Yarnell (57) ABSTRACT Methods are provided for predicting the properties of an asphalt fraction that contains two or more asphalt components based on measurements of the viscosity versus temperature profile for the components of the asphalt fraction. The viscosity versus temperature profile for each component can be used to determine characteristic (such as limiting) values for the viscosity and temperature for a component. Based on this ability to determine characteristic values for an asphalt blend based on the properties of individual blend components, appropriate blends of asphalts can be selected in order to arrive at an asphalt blend with desired properties.

5 Claims, 2 Drawing Sheets

Related U.S. Application Data (60) Provisional application No. 61/925,377, filed on Jan. 9, 2014.

(51) Int. Cl.
*C08J 3/00* (2006.01)
*G01N 11/00* (2006.01)

(52) U.S. Cl.
CPC ........ *C08J 2395/00* (2013.01); *C08J 2495/00* (2013.01); *C08L 2205/025* (2013.01); *C08L 2555/10* (2013.01); *G01N 11/00* (2013.01)

(58) Field of Classification Search
CPC ........ C10C 3/005; C09D 195/00; D06N 5/00; G01N 11/00
See application file for complete search history.

(56) References Cited

U.S. PATENT DOCUMENTS

| | | | |
|---|---|---|---|
| 4,282,038 A | 8/1981 | Earing | |
| 4,290,816 A | 9/1981 | Ludwig et al. | |
| 4,456,523 A * | 6/1984 | Carlos | C10C 3/04 208/22 |
| 4,874,432 A | 10/1989 | Kriech et al. | |
| 5,284,509 A * | 2/1994 | Kamel | C08L 95/00 106/273.1 |
| 5,695,555 A * | 12/1997 | Kamel | C08L 95/00 106/279 |
| 6,258,255 B1 * | 7/2001 | Gale | C10C 3/06 208/304 |
| 6,534,318 B2 * | 3/2003 | Roussis | G01N 33/28 436/139 |
| 10,005,907 B2 | 6/2018 | Sirota et al. | |
| 2014/0338565 A1 | 11/2014 | Severance et al. | |

FOREIGN PATENT DOCUMENTS

| FR | 44721 E | 4/1935 |
|---|---|---|
| JP | 2007211173 A | 8/2007 |

* cited by examiner

SELECTION AND BLENDING OF FEEDS FOR ASPHALT MANUFACTURE

CROSS REFERENCE TO RELATED APPLICATIONS

This application is a divisional application filed under 37 C.F.R. 1.53(b) of parent application Ser. No. U.S. 14/576,281, the entirety of which is hereby incorporated herein by reference, and claims priority to U.S. Non-Provisional Patent Application Ser. No. 14/576,281 filed on Dec. 19, 2014, which claims priority to U.S. Provisional Application Ser. No. 61/925,377 filed on Jan. 9, 2014, herein also incorporated by reference in its entirety.

FIELD

Methods are provided for predicting properties for asphalts formed from blends of feedstocks.

BACKGROUND

Asphalt is one of the world's oldest engineering materials, having been used since the beginning of civilization. Asphalt is a strong, versatile and chemical-resistant binding material that adapts itself to a variety of uses. For example, asphalt is used to bind crushed stone and gravel into firm tough surfaces for roads, streets, and airport runways. Asphalt, also known as pitch, can be obtained from either natural deposits, or as a by-product of the petroleum industry. Natural asphalts were extensively used until the early 1900s. The discovery of refining asphalt from crude petroleum and the increasing popularity of the automobile served to greatly expand the asphalt industry. Modern petroleum asphalt has the same durable qualities as naturally occurring asphalt, with the added advantage of being refined to a uniform condition substantially free of organic and mineral impurities.

The raw material used in modern asphalt manufacturing is petroleum, which is naturally occurring liquid bitumen. Asphalt is a natural constituent of petroleum, and there are crude oils that are almost entirely asphalt. The crude petroleum is separated into its various fractions through a distillation process. After separation, these fractions are further refined into other products such as asphalt, paraffin, gasoline, naphtha, lubricating oil, kerosene and diesel oil. Since asphalt is the base or heavy constituent of crude petroleum, it does not evaporate or boil off during the distillation process. Asphalt is essentially the heavy residue of the oil refining process.

Because asphalt is a residue from an oil refining process, if a blend of oils from more than one crude source is used as an input, the resulting asphalt residue will also represent a combination of the oils. Due to lower reliability of resulting asphalt quality prediction, proportions of individual crudes in the slate cannot be economized and a quality buffer is typically required. In the other words, a blend of feeds is selected that is conservative on quality, such as by using a higher percentage of heavy asphaltic feeds than is strictly needed, in order to increase the likelihood of meeting the asphalts specifications after manufacturing is done. However, having to select a heavier blend of feeds to form a desired asphalt can cause difficulties in other parts of a refinery, as using the heavier crudes that typically produce higher quality asphalt can limit the distillation throughput for the refinery.

Although individual asphalts can be characterized relative to a cut point temperature for separating heavy oil from the asphalt residue, conventional methods of characterizing blends of asphalts have been only partially successful. As a result, when a blend of oils is used to form an asphalt, the asphalt is usually characterized experimentally to determine all or nearly all specifications that determine the suitability of an asphalt for various potential uses. During this characterization time, storage tanks or another means for holding the asphalt prior to sale are required. If sufficient storage is not available, it may result in the slowing or even stopping of one or more additional refinery processes until the asphalt can be characterized and assigned a grade for sale.

SUMMARY

In an aspect, a method for forming an asphalt blend is provided, the method including measuring two or more viscosities for a plurality of asphalt components, each measured viscosity being measured at a different temperature; determining a characteristic temperature value and a characteristic viscosity value for each of the plurality of asphalt components; selecting a target characteristic temperature value range and a target characteristic viscosity value range for an asphalt blend; and forming an asphalt blend from the plurality of asphalt components, a volume percentage for each asphalt component in the asphalt blend being selected based on the target characteristic temperature value range and the target characteristic viscosity value range, wherein at least 50 vol % of the asphalt components in the asphalt blend have a) a characteristic temperature that differs from the target characteristic temperature value range by at least 10 Kelvin, b) a characteristic viscosity that differs from the target characteristic viscosity value range by at least 25%, or a combination of a) and b).

In another aspect, a method for forming an asphalt blend is provided, the method including measuring two or more viscosities for a plurality of asphalt components, each measured viscosity being measured at a different temperature; determining a characteristic temperature value and a characteristic viscosity value for each of the plurality of asphalt components; selecting a target characteristic temperature value range and a target characteristic viscosity value range for an asphalt blend, the target characteristic temperature value range and the target characteristic viscosity value range corresponding to a high temperature performance grade and a low temperature performance grade; and forming an asphalt blend from the plurality of asphalt components, a volume percentage for each asphalt component in the asphalt blend being selected based on the target characteristic temperature value range and the target characteristic viscosity value range, wherein at least 50 vol % of the asphalt components in the asphalt blend have c) a component high temperature performance grade that differs from the target characteristic temperature value range by at least 10 Kelvin, d) a component low temperature performance grade that differs from the target characteristic temperature value range by at least 10 Kelvin, e) a component high temperature performance grade that differs from the target characteristic viscosity value range by at least 25%, f) a component low temperature performance grade that differs from the target characteristic viscosity value range by at least 25%, or a combination of two or more of c), d), e), and f).

In still another aspect, a method for forming an asphalt blend is provided, the method including: obtaining a characteristic temperature value and a characteristic viscosity value for each of a plurality of asphalt components; selecting a target characteristic temperature value range and a target characteristic viscosity value range for an asphalt blend, the target characteristic temperature value range and the target characteristic viscosity value range corresponding to an asphalt having at least a first target asphalt property value range and a second target asphalt property value range; and forming an asphalt blend from the plurality of asphalt components, a volume percentage for each asphalt component in the asphalt blend being selected based on the target characteristic temperature value range and the target characteristic viscosity value range, wherein 35 vol % or less of the asphalt components in the asphalt blend have g) a component first target asphalt property value that differs from the first target asphalt property value range by 5% or less, h) a component second target asphalt property value that differs from the second target asphalt property value range by at least 5% or less, i) a characteristic temperature that differs from the target characteristic temperature value range by 10 Kelvin or less, j) a characteristic viscosity that differs from the target characteristic viscosity value range by 10% or less, or a combination of a plurality of g), h), i) and j).

DETAILED DESCRIPTION

All numerical values within the detailed description and the claims herein are modified by "about" or "approximately" the indicated value, and take into account experimental error and variations that would be expected by a person having ordinary skill in the art.

Overview

In various aspects, methods are provided for predicting the properties of an asphalt fraction that contains two or more asphalt components based on measurements of the viscosity versus temperature profile for the components of the asphalt fraction. The viscosity versus temperature profile for each component can be used to determine characteristic (such as limiting) values for the viscosity and temperature for a components. Examples of characteristic values for an asphalt component are the asymptotic values of viscosity at infinite temperature ($\eta_{inf}$) and the finite temperature at which the viscosity diverges ($T_0$). Once these characteristic values are determined, the characteristic values for each component can be combined in a weighted average to determine $\eta_{inf}$ and $T_0$ for the asphalt blend. Based on this ability to determine $\eta_{inf}$ and $T_0$ for an asphalt blend based on the properties of individual blend components, appropriate blends of asphalts can be selected in order to arrive at an asphalt blend with desired properties. Preferably, an asphalt blend with desirable properties can be formed while reducing or minimizing the amount of asphalt component(s) that already have $\eta_{inf}$ and $T_0$ values within the desired range. This allows for formation of a desired grade of asphalt from a variety of feeds with properties that are normally not considered as suitable for use in the desired grade.

For lighter fractions derived from a crude oil, blending tools can often provide useful predictions about the properties of blends containing components from a plurality of sources. This is in part due to the fact that lighter fractions have a relatively low number of distinct species. Additionally, blends of lighter fractions tend to have minimal amounts of non-linear interactions between components within the fractions. By contrast, the properties of a blend of asphalt fractions are difficult to predict based on a simple linear combination of the properties of individual asphalt fractions at a given temperature. The compositions of asphalt fractions often include a large number of species that may not be well understood. Additionally, due to the complexity of asphalt fractions, the plurality of asphalt fractions within a blend can have significant interactions.

Preferably, the properties for an asphalt fraction containing multiple asphalt components can be predicted based on a readily available test that allows for derivation of the desired properties based on the properties of the individual components. In various aspects, this can be accomplished by measuring a dynamic viscosity or a kinematic viscosity at a plurality of temperatures. The plurality of data points for a component can then be used to generate the asymptotic limit values for the viscosity and temperature relationship, which are referred to as $\eta_{inf}$ (viscosity) and $T_0$ (temperature). This allows for determination of $\eta_{inf}$ and $T_0$ for an asphalt blend based on the volumes of the individual components in the blend.

Figure 1:
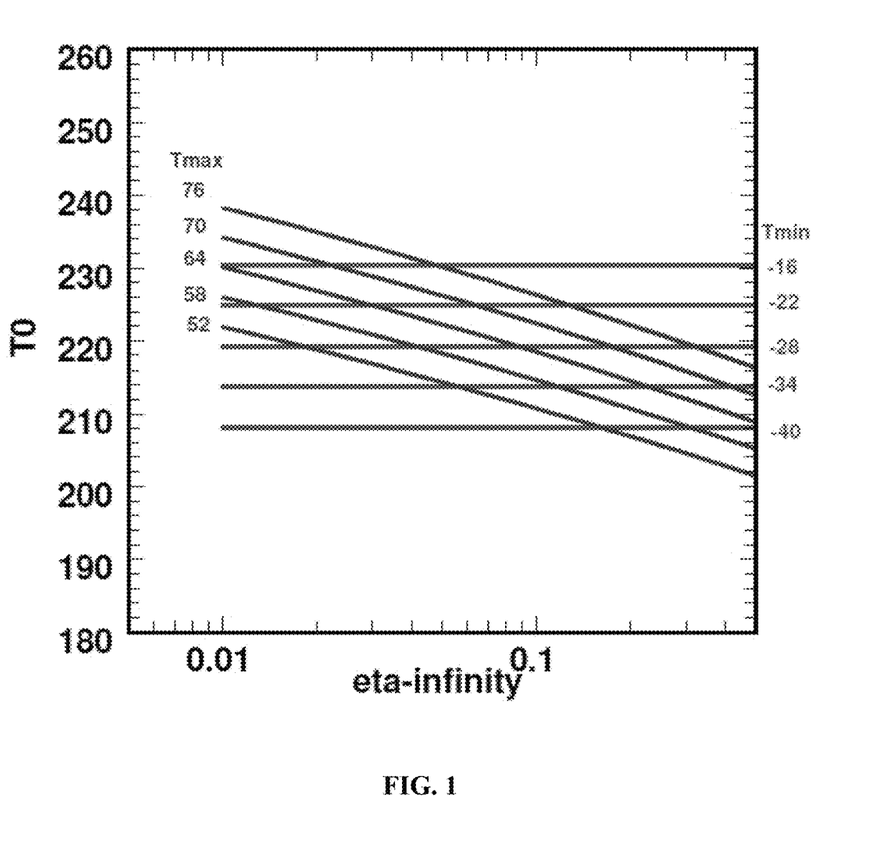
FIG. 1 shows an example of a correlation between performance grade temperatures for an asphalt and the $T_0$ and $\eta_{inf}$ values for an asphalt.

In order to use the model, an asphalt with a desired combination of $\eta_{inf}$ and $T_0$ can first be identified. One example of how to identify a desired asphalt composition is to select a combination of $\eta_{inf}$ and $T_0$ that correspond to a desired combination of high temperature performance grade and low temperature performance grade, such as temperatures corresponding to a location or box on a SUPERPAVE™ matrix. FIG. 1 shows an example of a correlation between $\eta_{inf}$ and $T_0$ values for an asphalt or asphalt blend and corresponding high temperature performance grades (shown as $T_{max}$ values in FIG. 1) and low temperature performance grades (shown as $T_{min}$ values in FIG. 1). The performance grade temperature values are plotted relative to $T_0$(Kelvin) $\eta_{inf}$(poise). It is noted that $\eta_{inf}$ is plotted on a log scale. In FIG. 1, the $T_{max}$ line and $T_{min}$ line are defined as $$T_0 = (T_{MAX} + 273.15)/(\ln 100000 - \ln \eta_{inf}) \quad (1)$$

$$T_0 = 220 + (T_{MIN} + 27.21)/1.076 \quad (2)$$

As an example, based on FIG. 1, if an asphalt blend is desired with a performance grade of 64-22, suitable blends can range from a) a blend with a $T_0$ of about 225 K and an $\eta_{inf}$ of about 0.02 to b) a blend with a $T_0$ of about 220 K and an $\eta_{inf}$ of about 0.18. Of course, other values within the parallelogram defined the $T_{max}$ lines for the high temperature performance grades of 64 and 70 and the low temperature performance grades of −22 and −28 can also be selected. Those of skill in the art recognize that selection of an asphalt performance grade is a description of a range of temperature values for both the high temperature performance grade and the low temperature performance grade, as opposed to a specification of a single combination of temperatures.

More generally, an asphalt with a desired combination of $\eta_{inf}$ and $T_0$ can be identified based on any convenient set of one or more asphalt properties. Examples of suitable properties for characterizing a desired asphalt include a penetration value based on a penetration test, such as ASTM D946 or D-5; any desired type of viscosity, such as kinematic viscosities, shear viscosities, or other convenient types of viscosities; a softening point for an asphalt, such as the softening point test specified by ASTM D3461; or any other convenient type of characteristic that is conventionally used for describing or specifying an asphalt. Preferably, a desired asphalt property can be specified based on a range of desired values for the property. Such a target property value range can be specified, for example, based on a low end range value and a high end range value that define the range. Another option for specifying a target property value range can be to specify a single value with a tolerance range or an error bar range. Still other options for specifying a target property value range to define a desired target asphalt will be readily apparent to those of skill in the art.

In this discussion, when a description is provided of a potential asphalt component having a property value different from a desired asphalt property value range by at least an amount, it is understood that the potential asphalt component has a property value that differs from any value within the range defined by the low end range value and the high end range value. Thus, a potential asphalt component with a property value that differs from a desired property value corresponds to a potential asphalt component with a property value that is outside of the range defined by the low end range value and the high end range value. As an example, when a potential asphalt component is described as having a high temperature performance value that differs from the desired high temperature performance value, it is understood that the potential asphalt component has a high temperature performance value that is outside of the range of temperatures that correspond to the desired high temperature performance value. In other words, if the desired high temperature performance value is 64° C., which corresponds to asphalts with a measured high temperature performance value of at least 64° C. but less than 70° C., a potential asphalt component that differs from the desired high temperature performance value will have a measured high temperature performance value that is either less than 64° C. or greater than 70° C.

In this discussion, reference will be made to asphalt fractions or components. An asphalt fraction or component represents an asphalt fraction made in any convenient manner, such as an asphalt fraction formed by distillation of a suitable feedstock at a suitable cut point temperature, or a suitable fraction generated by another type of refinery process. It is noted that an asphalt fraction or component as defined herein may include some fractions not traditionally considered as asphalt, such as brightstock extracts, so long as a $T_0$ value and an $\eta_{inf}$ can be determined for the fraction. More generally, so long as a $T_0$ value (or another characteristic temperature) and an $\eta_{inf}$ value (or another characteristic viscosity) can be determined, the model can be applied to any convenient type of fraction or component. Thus, formation of blends of fractions or components to form a non-asphaltic material can be assisted using the model described herein, so long as the fractions or components can be characterized in terms of a characteristic temperature (such as $T_0$ or an equivalent value) and a characteristic viscosity (such as $\eta_{inf}$).

Asphalt Feedstocks

Some feedstocks in accordance with the present disclosure are heavy oils that include at least a portion of asphaltenes. Such heavy oils are suitable, possibly after additional distillation, for making an asphalt. Asphalt is a semi-solid bituminous material derived from the distillation residue of crude petroleum. Asphalt may be obtained from a variety of crude oil sources or fractions, including straight run vacuum residue, mixtures of vacuum residue with diluents such as vacuum tower wash oil, paraffin distillate, aromatic and naphthenic oils and mixtures thereof, oxidized vacuum residues or oxidized mixtures of vacuum residues and diluent oils and the like. Because it is hydrophobic and has good adhesive and weathering characteristics, asphalt is widely used as a binder or cement for stone or rock aggregate in pavement construction (typically only about 5 wt % of the mixture). Other feedstocks suitable for use in the disclosure include whole or reduced petroleum crude oils, atmospheric residua feedstocks, and vacuum residua feedstocks.

One way of defining a feedstock is based on the boiling range of the feed. One option for defining a boiling range is to use an initial boiling point for a feed and/or a final boiling point for a feed. Another option, which in some instances may provide a more representative description of a feed, is to characterize a feed based on the amount of the feed that boils at one or more temperatures. For example, a "T5" boiling point for a feed is defined as the temperature at which 5 wt % of the feed will boil off. Similarly, a "T95" boiling point is a temperature at 95 wt % of the feed will boil. The percentage of a feed that will boil at a given temperature can be determined, for example, by the method specified in ASTM D2887.

A typical feedstock for forming asphalt can have a normal atmospheric boiling point of at least about 350° C., more typically at least 400° C., and will have a penetration range from 20 to 500 dmm at 25° C. (ASTM D-5). Alternatively, a feed may be characterized using a T5 boiling point, such as a feed with a T5 boiling point of at least about 350° C., or at least about 400° C., or at least about 440° C.

Another example of a feedstock suitable for forming asphalt is a feedstock derived from an atmospheric resid fraction or a similar petroleum fraction. For example, when a whole crude oil, partial crude oil, or other feedstock is processed in a refinery, one common type of processing is to distill or fractionate the crude oil based on boiling point. One type of fractionation is atmospheric distillation, which can result in one or more fractions that boil at less than about 650° F. (343° C.) or less than about 700° F. (371° C.), and a bottoms fraction. This bottoms fraction corresponds to an atmospheric resid.

The bottoms fraction from atmospheric distillation can then be separated or fractionated using vacuum distillation. This generates one or more (vacuum) gas oil fractions and a vacuum resid fraction. Because the vacuum distillation is typically performed on a resid from atmospheric distillation, a vacuum gas oil fraction can be defined as a fraction with a T10 boiling point of at least about 650° F. (343° C.), such as at least about 700° F. (371° C.). Preferably, a vacuum gas oil fraction can have a T5 boiling point of at least about 650° F., such as at least about 700° F. The vacuum resid fraction may be suitable for use as an asphalt. The distillation cut point for forming the vacuum bottoms fraction can be selected based on a desired amount of vacuum gas oil and/or a desired quality for the asphalt fraction. Selecting a higher temperature cut point can increase the amount of a vacuum gas oil. However, such a higher temperature cut point will typically reduce the quality of the corresponding asphalt. Since both vacuum gas oil yield and asphalt quality are also dependent on the nature of the feedstock, the temperature cut point to achieve a desired combination of vacuum gas oil yield and asphalt quality will vary. A suitable cut point for the vacuum bottoms fraction to achieve a desired asphalt quality and/or to achieve a desired vacuum gas oil yield can be at least about 750° F. (399° C.), such as at least about 950° F. (510° C.) or at least about 1050° F. (566° C.).

In addition to asphalt fractions formed directly from a crude oil or crude fraction, other types of "asphalt" fractions can also be used. For example, aromatic extracts generated by solvent extraction of a distillate or brightstock fraction can be suitable for incorporation into an asphalt blend. Another suitable fraction can be the "rock" generated during deasphalting of a vacuum distillate or bottoms fraction. More generally, any fraction that can be meaningfully characterized in terms of a $T_0$ value and an $\eta_{inf}$ could potentially be used as a fraction.

Characterization of Asphalt Blend Components

In various aspects, the $T_0$ and $\eta_{inf}$ values for an asphalt blend component can be determined based on Equation (3).

$$\eta = \eta_{inf} e^{\left[\frac{D}{(T/T_0)-1}\right]} \quad (3)$$

In Equation (1), r is the viscosity at a temperature T. $\eta_{inf}$ and $T_0$ have the definitions provided above. In Equation (1), D is a constant that can be set based on historical data for asphalt fractions. While D can vary in practice, in Equation (3), sufficient accuracy can be achieved by setting D to a constant value that is representative of the $\eta_{inf}$ values that are typically encountered in asphalt blend components. In this discussion, D will be set to a constant value of 7.5. Other potential values for D could be selected while also giving suitable results, such as a constant value for D between about 5.0 to about 15.0, and preferably a constant value for D between about 6.5 to about 10.5.

In Equation (3), based on the use of a constant value for D, such as 7.5, for a given asphalt component, $\eta_{inf}$ and $T_0$ are the two values that need to be fit to experimental data. Thus, at least two measurements of the viscosity r at a temperature T are needed to fit values to $\eta_{inf}$ and $T_0$. In practice, additional measured values can be obtained for a given component in order to further improve the fit of Equation (3) to the data.

One option for obtaining viscosity values at different temperature for a component sample is to obtain Brookfield viscosity values at different temperatures. Preferably, the Brookfield viscosity values obtained for a component can be obtained using a single measurement device, so that any systematic errors in the measurement will be the same for all measured values on a component. Alternatively, other types of devices for measuring a kinematic viscosity at a temperature can be used to generate a plurality of viscosity values η at a plurality of temperatures T.

With regard to selecting temperatures for obtaining viscosity values, several factors can be considered. First, the viscosity values for a component can be obtained at temperatures where the component is above the wax melting temperature for the component and/or where the component is at a temperature where the component behaves as a Newtonian fluid. For asphalt fractions that have a high hardness value, it may be necessary to measure the viscosity at higher temperatures, such as at least about 130° C. or at least about 150° C. For many other types of asphalt fractions, a temperature of at least about 100° C. is sufficient for the asphalt fraction to act as a Newtonian fluid and/or be above the wax melting temperature. Another factor can be to have at least two data points within the set of data for fitting the $\eta_{inf}$ and $T_0$ values that are at least about 10° C. apart. If the temperatures for all of the viscosity values in the data set are grouped too closely together, the quality of the parameter fit may be reduced.

After obtaining two or more viscosity and temperature data point pairs for an asphalt component, the $\eta_{inf}$ and $T_0$ can be calculated by fitting the data points to the functional form shown in Equation (3). This process can be repeated for each desired asphalt component that is to be included in an asphalt blend. Additionally or alternately, the $\eta_{inf}$ and $T_0$ values for one or more asphalt components in a blend can be determined based on fitting Equation (3) to previously obtained or published data for a component. This previously obtained or published data can correspond to viscosity and temperature values as described above, or the prior data can correspond to other data that allows for calculation of a viscosity at a plurality of temperatures.

One variation on the model is that the glass transition temperature ($T_g$) for a group of asphalt components to be used in an asphalt blend can be used in place of $T_0$ if desired. The procedure for fitting measured data to Equation (3) and subsequent use of the $T_g$ and $\eta_{inf}$ values is otherwise similar.

Predicting Asphalt Properties Based on Blend Components

Based on $T_0$ and $\eta_{inf}$ values for a plurality of components, the $T_0$ and $\eta_{inf}$ value for an asphalt blend can be determined. An advantage of using $T_0$ and $\eta_{inf}$ to characterize the components of an asphalt blend is that the values can be used in a weighted average to determine the $T_0$ and $\eta_{inf}$ value for the resulting blend. In particular, the $T_0$ value of a blend of asphalt components can be determined by Equation (4). The $\eta_{inf}$ value of a blend of asphalt components can similarly be determined by Equation (5).

$$T_0 = \Sigma_i \varnothing_i T_{0,i} \quad (4)$$

$$\ln \eta_{inf} = \Sigma_i \varnothing_i \ln \eta_{inf,i} \quad (5)$$

In Equations (4) and (5), $\varnothing_i$ corresponds to the volume percent of component "i" in an asphalt blend. As shown in Equations (4) and (5), the $T_0$ values can be combined as a weighted average of the $T_0$ values of the components, while the $\eta_{inf}$ values can be combined as a weighted average of a log of the $\eta_{inf}$ values of the components.

After determining the $T_0$ and $\eta_{inf}$ values for an asphalt blend based on the volumes of the components in the blend, the $T_0$ and $\eta_{inf}$ values can be used to determine other properties of the asphalt blend, such as a target asphalt property value or value range. For example, the high performance temperature grade and low performance temperature grade curves shown in FIG. 1 represent correlations developed based on measurements of $T_0$ and $\eta_{inf}$ for various asphalt compositions. In some aspects, the high temperature performance grade for an asphalt can represent a first target asphalt property value range while a low temperature performance grade can represent a second target asphalt property value range. Of course, other properties of an asphalt can be selected as target asphalt property values instead of and/or in addition to performance grades. More generally, it is believed that a variety of properties can be correlated with $T_0$ and $\eta_{inf}$ values for an asphalt or asphalt blend. For example, the PEN (needle penetration) value for an asphalt is believed to be correlated with the $T_0$ and $\eta_{inf}$ values. In order to provide a general correlation with other properties, such as the softening point for an asphalt, it is believed that the wax content of the resulting asphalt blend can be included into the correlation. Penetration values and softening point values represent examples of other properties that can correspond to target asphalt property values for determination using the methods provided herein.

Formation of Non-Traditional Asphalt Blends

One feature of being able to characterize an asphalt blend based on the $T_0$ and $\eta_{inf}$ values of the components in the blend is the ability to form an asphalt blend having a desired feature while reducing or minimizing the amount of any components in the blend that already have the desired feature. In conventional asphalt blends, it is believed to be necessary to use components in the blend that have a desired property as the majority of components in the blend. For example, if an asphalt blend is desired that has a 64-22 combination of high temperature and low temperature performance grade, using conventional blending methods, it is believed to be necessary to have at least 50 wt % of the blend correspond to components that meet the desired 64-22 performance grade specification.

By contrast, using the $T_0$ and $\eta_{inf}$ values of components in a blend to determine the $T_0$ and $\eta_{inf}$ values for the blend can allow for formation of asphalt blends with components that would traditionally be viewed as less desirable. For example, with regard to performance grades, in some aspects asphalt blends can be formed where components corresponding to at least about 50 vol % of the asphalt blend have a high temperature and/or low temperature performance grade that does not meet the desired specification, such as at least about 60 vol % can have a high temperature and/or low temperature performance grade that does not meet the desired specification, or at least about 70 vol %. As described herein, an asphalt component that does not meet a desired performance grade is an asphalt component with a measured value for the high temperature performance and/or low temperature performance that is outside of the range corresponding to the performance grade. Thus, for a desired high temperature performance grade of 58° C., an asphalt component that does not meet this desired specification can have a measured high temperature performance of less than 58° C. or at least 64° C. Similarly, for a desired low temperature performance grade of −16° C., an asphalt component that does not meet this desired specification can have a measured low temperature performance grade of greater than −16° C. or less than −22° C.

Another feature of using the $T_0$ and $\eta_{inf}$ values of components to determine $T_0$ and $\eta_{inf}$ values for the resulting blend is that asphalt components with properties with lower similarity to the properties of a desired asphalt can be incorporated. In conventional blending, because it is believed that the majority of the blend components should have the desired properties for the blend, it can be difficult to blend in meaningful amounts of components that differ substantially from the desired blend properties. By contrast, by using the $T_0$ and $\eta_{inf}$ values of the components to determine the $T_0$ and $\eta_{inf}$ values for the blend, components with disparate properties can be included in a blend with the understanding that the disparate properties will average out to produce $T_0$ and $\eta_{inf}$ values within the desired specification. In some aspects, the difference between the properties of a component and the properties of a resulting asphalt blend can be based on a difference in the $T_0$ and $\eta_{inf}$ values of the component in comparison with the blend. In such aspects, the difference between the $T_0$ of a component and the $T_0$ of an asphalt blend can be determined based on the $T_0$ values expressed in Kelvin In some aspects, the difference between the $\eta_{inf}$ of a component and the $\eta_{inf}$ of an asphalt blend can be determined based on natural log (or other log) values of $\eta_{inf}$. However, specifying a standard based on log values can lead to uncertainty, as the percentage difference between values for comparison can vary depending on the base used for performing the logarithm. Optionally but preferably, the difference between the $\eta_{inf}$ of a component and the $\eta_{inf}$ of an asphalt blend can be determined based on a comparison of the actual $\eta_{inf}$ values rather than the log values. In such aspects, at least about 25 vol % of the components in a blend can have at least one of a $T_0$ value or an $\eta_{inf}$ value that substantially differs from the desired and/or resulting $T_0$ and $\eta_{inf}$ values, such as at least about 35 vol % of the components or at least about 45 vol % of the components. For differences in a $T_0$ value (or differences between other values specified based on a temperature), a value that substantially differs from a desired $T_0$ value can correspond to a value that is different by more than 10 Kelvin, such as at least about 20 Kelvin, or at least about 25 Kelvin, or at least about 30 Kelvin, and optionally up to 100 Kelvin or less. A value that substantially differs from an $\eta_{inf}$ value can correspond to a value that is at least about 25% different, such as at least about 35% different, or at least about 50% different, or at least about 75% different.

In still other aspects, the difference between the properties of a component and the properties of a desired blend can be based on a difference in the high temperature performance grade and low temperatures performance grade values of a component in comparison with temperature grade values for the blend. In such aspects, the difference between the (high and/or low) temperature performance grade of a component and the (high and/or low) temperature performance grade of an asphalt blend can be determined based on temperature values expressed in Kelvin. In such aspects, at least about 25 vol % of the components in a blend can have at least one of a high temperature performance grade or a low temperature performance grade that substantially differs from the corresponding desired and/or resulting performance grade, such as at least about 35 vol % of the components or at least about 45 vol % of the components. A value that substantially differs from the desired and/or resulting high temperature performance grade or low temperature performance grade can correspond to a value that is at least about 10% different, such as at least about 15% different, or at least about 20% different, or at least about 25% different. More generally, the differences between component values for a target asphalt property can be compared with the desired values for the target asphalt property in an asphalt blend in a manner similar to that described above for performance grades. In such aspects, the percentage difference between component values for a target asphalt property and the desired range specification for the property can be a percentage difference when the property is expressed in the units conventionally used for describing the property.

In yet other aspects, the difference between the properties of a component and the properties of a desired blend can be based on a difference in the $T_0$ and $\eta_{inf}$ values of the component in comparison with the blend, where the amount of components that have $T_0$ and $\eta_{inf}$ values that are substantially similar to the $T_0$ and $\eta_{inf}$ values for the asphalt blend is reduced or minimized. In such aspects, the difference between the $T_0$ of a component and the $T_0$ of an asphalt blend can be determined based on the $T_0$ values expressed in Kelvin. The difference between the $\eta_{inf}$ of a component and the $\eta_{inf}$ of an asphalt blend can preferably be determined based on the values of $\eta_{inf}$, as opposed to a difference based on a log value of $\eta_{inf}$. In some aspects, about 50 vol % or less of the components in a blend can have a $T_0$ value that is substantially similar to the $T_0$ value for a resulting asphalt blend, such as about 35 vol % or less of the components, or about 25 vol % or less of the components. Additionally or alternately, in some aspects, about 50 vol % or less of the components in a blend can have an $\eta_{inf}$ value that is substantially similar to the $\eta_{inf}$ value for a resulting asphalt blend, such as about 35 vol % or less of the components, or about 25 vol % or less of the components. A value that is substantially similar to a $T_0$ value can correspond to a value that differs by about 10 Kelvin or less, such as about 5

Kelvin or less. A value that is substantially similar to a $\eta_{inf}$ value can correspond to a value that differs by about 10% or less, such as about 5% or less.

Example of Forming Desired Asphalt Blend from Asphalt Components

Figure 2:
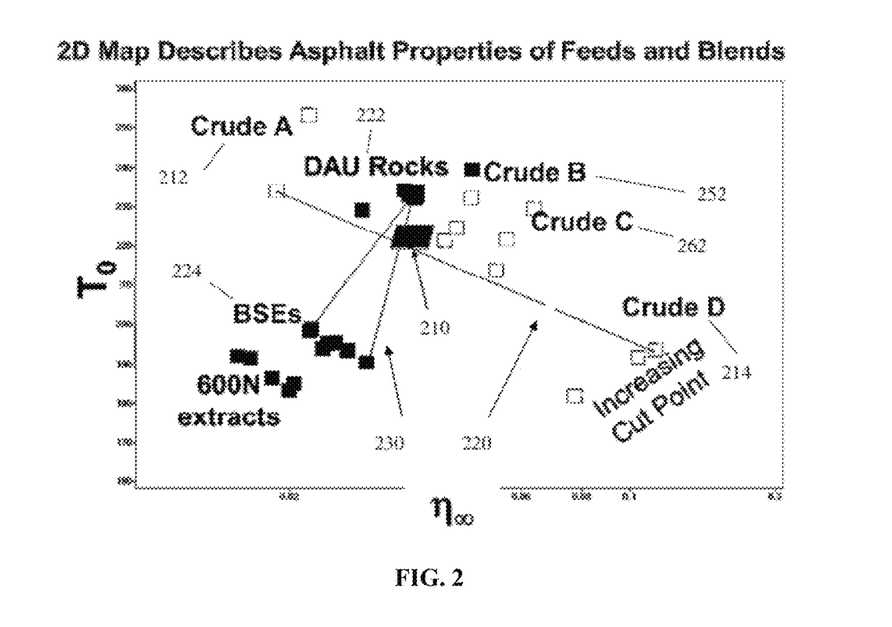
FIG. 2 shows an example of $T_0$ and $\eta_{inf}$ values for various potential asphalt components in relation to a target asphalt blend.

FIG. 2 shows examples of a variety of potential asphalt fractions that potentially can be included in an asphalt. The x-axis in FIG. 2 corresponds to the $\eta_{inf}$ value (on a log scale) of a potential blend component while the y-axis corresponds to the $T_0$ value. In FIG. 2, four different types of vacuum resid feeds are shown as potential blend components. These vacuum resid feeds are labeled as Crudes A, B, C, and D. For each Crude, a trend line shows potential vacuum resids that could be generated from the Crude by varying the distillation cut point in a vacuum distillation unit for separating the vacuum resid from the distillate portion of the crude. Some additional blend components in the form of deasphalting unit Rock feeds (DAU Rocks), brightstock extracts (BSEs), and 600N extracts are shown. Each square represents an actual feed that could be used in order to make an asphalt blend.

FIG. 2 also depicts an area 210 corresponding to asphalt blends with desired combinations of $T_0$ and $\eta_{inf}$. Any convenient combination of components shown in FIG. 2 that results in weighted averages of $T_0$ and $j\eta_{inf}$ within the area 210 can be used to make a desired asphalt blend. One simple way to visualize such combinations is to use combinations of blend components where a line can be drawn from a first blend component to a second blend component, and that line passes through the desired area 210. Those of skill in the art understand that being able to draw such a line is not required, but that is merely simplifies the calculation of how much of each blend component to include for blend components that have such a relationship. In FIG. 2, a vacuum resid 212 formed from Crude A and a vacuum resid 214 formed from Crude D share such a relationship, as shown by line 220. Similarly, a DAU Rock component 222 and a Brightstock Extract component 224 share such a relationship as shown by line 230.

In FIG. 2, line 220 crosses through area 210 at a location that is approximately two-thirds of the distance from the Crude D fraction 214 to the Crude A fraction 212 along the line. Thus, if a two to one ratio of the Crude A fraction 212 to the Crude D fraction 214 is maintained, the resulting mixture or blend of Crude A and Crude D should remain within the area 210, indicating formation of an asphalt blend with desired properties. Similarly, the line 230 connecting the DAU Rock component 222 with the BSE component 224 is about three fourths of the distance along the line from the BSE fraction 224 to the DAU Rock fraction 222. Thus, if a three to one ratio of the DAU Rock component to the BSE component is maintained, the resulting blend of DAU Rock and BSE should remain within area 210.

For convenience, an example of formation of an asphalt blend is provided, where the $T_0$ and $\eta_{inf}$ values for the blend correspond to the location 246 in area 210 where lines 220 and 230 cross. The blend components for forming the blend are components 222, 224, 232, and 234. Table 1 shows the $T_0$ and $\eta_{inf}$ values for the desired blend 246 and components 222, 224, 232, and 234. The corresponding $\log_{10}$ values for each $\eta_{inf}$ are also provided. As shown in Table 1, the $\eta_{inf}$ value for the resid from Crude A differs from the target blend value by at least about 50%, while the $\eta_{inf}$ value for the resid from Crude D differs from the target blend values by more than 75%. The $T_0$ value for the resid from Crude D and for the brightstock extract also differs from the target asphalt by at least about 25 Kelvin.

TABLE 1

Asphalt Component and Blend Values

| | $T_0$ (Kelvin) | $\eta_{inf}$ | $\log_{10} \eta_{inf}$ |
|---|---|---|---|
| Target asphalt blend (246) | 220-225 | 0.036 to 0.040 | -1.40 to -1.44 |
| Resid from Crude A (222) | 235 | 0.020 | -1.70 |
| Resid from Crude D (224) | 195 | 0.106 | -0.97 |
| DAU Rock (232) | 235 | 0.042 | -1.38 |
| Brightstock Extract (234) | 190 | 0.029 | -1.54 |

Based on the values from Table 1, a desired asphalt blend can be created by forming a blend of 50 vol % resid from Crude A 222, 25 vol % resid from Crude D 224, 18 vol % DAU Rock 232, and 6 vol % brightstock extract 234. Such an asphalt blend includes more than 50 vol % of components that substantially differ (i.e., by at least 10%, or at least 20%) from the $T_0$ and $\eta_{inf}$ values for the asphalt blend.

It is noted that the weight percentages listed add up to 99 vol %. The remaining 1 wt % could be composed of the Crude A, Crude D, DAU Rock, and brightstock extract components in the same ratios. Alternatively, if an asphalt blend closer to the center of area 210 is desired, the remaining 1 vol % could be satisfied by adding 1 vol % of either vacuum resid 252 from Crude B or 1 vol % of vacuum resid 262 from Crude C. More generally, any other amount of other components to create an asphalt blend within the desired area 210.

Applications for Predictive Model

The ability to predict properties for an asphalt fraction containing multiple asphalt components based on two derived viscosity and temperature parameters allows the predictive model to be applied in a variety of situations. One option for using the model described above is to use the model to provide real-time feedback for an asphalt formation process. One advantage of using the viscosity at a temperature between 100° C. and 150° C. as a measured property is that a viscosity can be obtained in a relatively short time with an in-line monitor. Thus, a plurality of viscosity values can be obtained at a convenient interval, such as once a minute. These viscosity values can be used to calculate $T_0$ and $\eta_{inf}$ values for the asphalt being produced, in order to verify that an asphalt within a desired specification is being produced and/or to provide feedback so that some aspect of the asphalt production process can be changed. Examples of potential changes include, but are not limited to, modifying a distillation cut point for forming a vacuum resid from a crude slate; modifying the composition of a crude slate; modifying the severity of an oxidation unit or another asphalt post-processing unit; or any other convenient modification. Because an asphalt fraction will often be at a higher temperature than the desired temperature for the viscosity measurement, a slip stream of the asphalt fraction can be withdrawn and cooled in order to obtain the viscosity measurements for calculating the $T_0$ and $\eta_{inf}$ values.

Another option is to use the predictive model to calculate the most suitable and/or economical crude slate. A number of available crudes can be selected. One or more target asphalt properties can also be specified. Optionally, limits on the weight fraction of each component can also be specified. The predictive model can then be used to calculate the weight fraction in order to meet the suggested requirements. The predictive model can also be used to maximize a component crude for a given slate (for instance the cheapest)

or minimize a component crude for a given slate (for instance minimizing the heaviest component to enhance throughput).

Additional Embodiments

Embodiment 1. A method for forming an asphalt blend, comprising: measuring two or more viscosities for a plurality of asphalt components, each measured viscosity being measured at a different temperature; determining a characteristic temperature value and a characteristic viscosity value for each of the plurality of asphalt components; selecting a target characteristic temperature value range and a target characteristic viscosity value range for an asphalt blend; and forming an asphalt blend from the plurality of asphalt components, a volume percentage for each asphalt component in the asphalt blend being selected based on the target characteristic temperature value range and the target characteristic viscosity value range, wherein at least 50 vol % of the asphalt components in the asphalt blend have a) a characteristic temperature that differs from the target characteristic temperature value range by at least 10 Kelvin, b) a characteristic viscosity that differs from the target characteristic viscosity value range by at least 25%, or a combination of a) and b).

Embodiment 2. The method of Embodiment 1, wherein at least 50 vol % of the asphalt components in the asphalt blend, or at least 60 vol %, or at least 70 vol %, have a) a characteristic temperature that differs from the target characteristic temperature value range by at least 15 Kelvin, or at least 20 Kelvin, or at least 25 Kelvin, or at least 30 Kelvin b) a characteristic viscosity that differs from the target characteristic viscosity value range by at least 35%, or at least 50%, or at least 75%, or a combination of a) and b).

Embodiment 3. The method of any of the above embodiments, wherein the target characteristic temperature value range and the target characteristic viscosity value range for the asphalt blend comprise a range of characteristic temperature values and characteristic viscosity values that correspond to a high temperature performance grade and a low temperature performance grade.

Embodiment 4. A method for forming an asphalt blend, comprising: measuring two or more viscosities for a plurality of asphalt components, each measured viscosity being measured at a different temperature; determining a characteristic temperature value and a characteristic viscosity value for each of the plurality of asphalt components; selecting a target characteristic temperature value range and a target characteristic viscosity value range for an asphalt blend, the target characteristic temperature value range and the target characteristic viscosity value range corresponding to a high temperature performance grade and a low temperature performance grade; and forming an asphalt blend from the plurality of asphalt components, a volume percentage for each asphalt component in the asphalt blend being selected based on the target characteristic temperature value range and the target characteristic viscosity value range, wherein at least 50 vol % of the asphalt components in the asphalt blend have c) a component high temperature performance grade that differs from the target characteristic temperature value range by at least 10 Kelvin, d) a component low temperature performance grade that differs from the target characteristic temperature value range by at least 10 Kelvin, e) a component high temperature performance grade that differs from the target characteristic viscosity value range by at least 25%, f) a component low temperature performance grade that differs from the target characteristic viscosity value range by at least 25%, or a combination of two or more of c), d), e), and f).

Embodiment 5. The method of Embodiment 3 or 4, wherein at least 50 vol % of the asphalt components in the asphalt blend, or at least 60 vol %, or at least 70 vol %, have c) a component high temperature performance grade that differs from the target characteristic temperature value range by at least 15 Kelvin, or at least 20 Kelvin, or at least 25 Kelvin, or at least 30 Kelvin, d) a component low temperature performance grade that differs from the target characteristic temperature value range by at least 10 Kelvin, or at least 20 Kelvin, or at least 25 Kelvin, or at least 30 Kelvin, e) a component high temperature performance grade that differs from the target characteristic viscosity value range by at least 35%, or at least 50%, or at least 75% f) a component low temperature performance grade that differs from the target characteristic viscosity value range by at least 35%, or at least 50%, or at least 75%, or a combination of two or more of c), d), e), and f), or a combination of three or more of c), d), e), and f), or a combination of c), d), e), and f).

Embodiment 6. The method of any of the above embodiments, wherein 35 vol % or less of the asphalt components in the asphalt blend, or 25 vol % or less, or 20 vol % or less, or 15 vol % or less, have g) a component first target asphalt property value that differs from the first target asphalt property value by 5% or less, h) a component second target asphalt property value that differs from the second target asphalt property value by at least 5% or less, i) a characteristic temperature that differs from the target characteristic temperature value range by 10 Kelvin or less, or 5 Kelvin or less, j) a characteristic viscosity that differs from the target characteristic viscosity value range by 10% or less, or 5% or less, or a combination of two or more of g), h), i) and j), or a combination of three or more of g), h), i) and j), or a combination of g), h), i) and j).

Embodiment 7. A method for forming an asphalt blend, comprising: obtaining a characteristic temperature value and a characteristic viscosity value for each of a plurality of asphalt components; selecting a target characteristic temperature value range and a target characteristic viscosity value range for an asphalt blend, the target characteristic temperature value range and the target characteristic viscosity value range corresponding to an asphalt having at least a first target asphalt property value range and a second target asphalt property value range; and forming an asphalt blend from the plurality of asphalt components, a volume percentage for each asphalt component in the asphalt blend being selected based on the target characteristic temperature value range and the target characteristic viscosity value range, wherein 35 vol % or less of the asphalt components in the asphalt blend have g) a component first target asphalt property value that differs from the first target asphalt property value range by 5% or less, h) a component second target asphalt property value that differs from the second target asphalt property value range by at least 5% or less, i) a characteristic temperature that differs from the target characteristic temperature value range by 10 Kelvin or less, j) a characteristic viscosity that differs from the target characteristic viscosity value range by 10% or less, or a combination of a plurality of g), h), i) and j).

Embodiment 8. The method of Embodiment 7, wherein 25 vol % or less of the asphalt components in the asphalt blend, or 20 vol % or less, or 15 vol % or less, have g) a component first target asphalt property value that differs from the first target asphalt property value range by 5% or less, h) a component second target asphalt property value that differs from the second target asphalt property value range by at least 5% or less, i) a characteristic temperature that differs from the target characteristic temperature value range by 10 Kelvin or less, or 5 Kelvin or less, j) a characteristic viscosity that differs from the target characteristic viscosity value range by 10% or less, or 5% or less, or a combination of two or more of g), h), i) and j), or a combination of three or more of g), h), i) and j), or a combination of g), h), i) and j).

Embodiment 9. The method of Embodiment 7 or 8, wherein the first target asphalt property value range comprises a high temperature performance grade and the second target asphalt property value range comprises a low temperature performance grade.

Embodiment 10. The method of any of Embodiments 7 to 9, wherein selecting a first target asphalt property value range comprises selecting a first property value and a first tolerance range, wherein selecting a second target asphalt property value range comprises selecting a second property value and a second tolerance range, or a combination thereof.

Embodiment 11. The method of any of the above embodiments, wherein selecting a first target asphalt property value range comprises selecting a first low range end value and a first high range end value for the first target asphalt property value range, wherein selecting a second target asphalt property value range comprises selecting a second low range end value and a second high range end value for the second target asphalt property value range, or a combination thereof.

Embodiment 12. The method of any of the above embodiments, wherein determining a characteristic temperature value and a characteristic viscosity value for each of the plurality of asphalt components comprises fitting the measured values for each of the plurality of asphalt components to an equation having the form $$\eta = \eta_{inf} e^{\left[\left[(T/T_0)-1\right]\right]}$$

where $\eta_{inf}$ is the characteristic viscosity, $T_0$ is the characteristic temperature, $\eta$ and $T$ are the measured values, and $D$ is a predetermined constant.

Embodiment 13. The method of any of the above embodiments, wherein the characteristic temperature is selected from $T_0$ or $T_g$, wherein the characteristic viscosity is $\eta_{inf}$, or a combination thereof.

Embodiment 14. The method of any of the above embodiments, wherein selecting a target characteristic temperature value range comprises selecting a low range end value and a high range end value for the target characteristic temperature value range, wherein selecting a target characteristic viscosity value range comprises selecting a low range end value and a high range end value for the target characteristic viscosity value range, or a combination thereof.

Embodiment 15. The method of any of Embodiments 1 to 14, wherein selecting a target characteristic temperature value range comprises selecting a temperature value and a tolerance range, wherein selecting a target characteristic viscosity value range comprises selecting a viscosity value and a tolerance range, or a combination thereof.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A method for forming an asphalt blend, comprising:
measuring two or more viscosities for a plurality of asphalt components, each measured viscosity being measured at a different temperature to form a plurality of data points for each of the plurality of asphalt components
obtaining a characteristic temperature value and a characteristic viscosity value for each of the plurality of asphalt components by using the plurality of data points for each of the plurality of asphalt components to generate asymptotic limit values to form a viscosity ($\eta_{inf}$) and temperature ($T_0$) relationship;
selecting a target characteristic temperature value range and a target characteristic viscosity value range for an asphalt blend, the target characteristic temperature value range and the target characteristic viscosity value range corresponding to an asphalt having at least a first target asphalt property value range and a second target asphalt property value range; and
forming an asphalt blend from the plurality of asphalt components, a volume percentage for each asphalt component in the asphalt blend being selected based on the target characteristic temperature value range and the target characteristic viscosity value range using the viscosity ($\eta_{inf}$) and temperature ($T_0$) relationship,
wherein 35 vol % or less of the asphalt components in the asphalt blend have g) a component first target asphalt property value that differs from the first target asphalt property value by 5% or less, h) a component second target asphalt property value that differs from the second target asphalt property value by 5% or less, i) a characteristic temperature that differs from the target characteristic temperature value range by 10 Kelvin or less, j) a characteristic viscosity that differs from the target characteristic viscosity value range by 10% or less, or a combination of a plurality of g), h), i) and j).

2. The method of claim 1, wherein 25 vol% or less of the asphalt components in the asphalt blend have g) a component first target asphalt property value that differs from the first target asphalt property value by 5% or less, h) a component second target asphalt property value that differs from the second target asphalt property value by 5% or less, i) a characteristic temperature that differs from the target characteristic temperature value range by 10 Kelvin or less, j) a characteristic viscosity that differs from the target characteristic viscosity value range by 10% or less, or a combination of a plurality of g), h), i) and j).

3. The method of claim 1, wherein the characteristic temperature is selected from $T_0$ or $T_g$ and the characteristic viscosity is $\eta_{inf}$.

4. The method of claim 1, wherein the first target asphalt property value range comprises a high temperature performance grade and the second target asphalt property value range comprises a low temperature performance grade.

5. The method of claim 1, wherein determining a characteristic temperature value and a characteristic viscosity value for each of the plurality of asphalt components comprises fitting the measured values for each of the plurality of asphalt components to an equation having the form $$\eta = \eta_{inf} e^{\left[\left(T/T_0\right)-1\right]}$$

where $\eta_{inf}$ is the characteristic viscosity, $T_0$ is the characteristic temperature, $\eta$ and T are the measured values, and D is a predetermined constant.

* * * * *